(12) United States Patent
Chung et al.

(10) Patent No.: US 6,997,953 B2
(45) Date of Patent: Feb. 14, 2006

(54) METHOD FOR IMPLANTING A LAMINOPLASTY

(75) Inventors: Jae-Yoon Chung, Jisan-Dong (KR); Michael Carl Michielli, Medway, MA (US)

(73) Assignee: DePuy Spine, Inc., Raynham, MA (US)

( * ) Notice: Subject to any disclaimer, the term of this patent is extended or adjusted under 35 U.S.C. 154(b) by 0 days.

(21) Appl. No.: 10/762,840

(22) Filed: Jan. 22, 2004

(65) Prior Publication Data

US 2004/0153155 A1    Aug. 5, 2004

Related U.S. Application Data

(63) Continuation of application No. 10/260,329, filed on Sep. 30, 2002, now Pat. No. 6,712,852.

(51) Int. Cl.
*A61F 2/44* (2006.01)

(52) U.S. Cl. .................................................. 623/17.11

(58) Field of Classification Search ................. 606/61, 606/63, 76, 78; 623/17.11, 17.12, 17.13, 623/17.15, 17.16, 23.47, 23.5
See application file for complete search history.

(56) References Cited

U.S. PATENT DOCUMENTS

| | | |
|---|---|---|
| 5,147,402 A | 9/1992 | Bohler et al. |
| 5,192,327 A | 3/1993 | Brantigan |
| 5,258,031 A | 11/1993 | Salib et al. |
| 5,458,638 A | 10/1995 | Kuslich et al. |
| 5,496,318 A | 3/1996 | Howland et al. |
| 5,702,449 A | 12/1997 | McKay |
| 5,976,187 A | 11/1999 | Richelsoph |
| 6,001,130 A | 12/1999 | Bryan et al. |
| 6,074,423 A | 6/2000 | Lawson |
| 6,080,157 A | 6/2000 | Cathro et al. |
| 6,132,464 A | 10/2000 | Martin |
| 6,143,031 A | 11/2000 | Knothe et al. |
| 6,245,108 B1 | 6/2001 | Biscup |
| 6,302,914 B1 | 10/2001 | Michelson |
| 6,358,254 B1 | 3/2002 | Anderson |
| 6,375,655 B1 | 4/2002 | Zdeblick et al. |
| 6,419,703 B1 | 7/2002 | Fallin et al. |
| 6,419,705 B1 * | 7/2002 | Erickson .................. 623/17.16 |
| 6,423,095 B1 | 7/2002 | Van Hoeck et al. |
| 6,660,007 B1 * | 12/2003 | Khanna ....................... 606/61 |
| 2002/0120335 A1 | 8/2002 | Angelucci et al. |
| 2003/0045935 A1 | 3/2003 | Angelucci et al. |
| 2003/0045936 A1 | 3/2003 | Angelucci et al. |
| 2003/0093154 A1 | 5/2003 | Estes et al. |
| 2003/0100950 A1 | 5/2003 | Moret |

FOREIGN PATENT DOCUMENTS

| | | |
|---|---|---|
| DE | 197 38 052 A1 | 3/1999 |
| JP | 2000152951 | 6/2000 |
| JP | 2001170092 | 6/2001 |

* cited by examiner

*Primary Examiner*—Eduardo C. Robert
*Assistant Examiner*—David Cornstock
(74) *Attorney, Agent, or Firm*—Nutter, McClennen & Fish LLP

(57) ABSTRACT

A medical implant device for use in spinal surgery, and more preferably for use in laminoplasty surgery is provided. The implant is a cage-like member having a generally hollow, elongate body with open ends. The implant is formed from a generally hollow, elongate body having four sides: opposed cephalad and caudal sides, and opposed posterior and anterior sides adjacent to the cephalad and caudal sides. The four sides extend along a longitudinal axis, and define an inner lumen extending between opposed first and second open ends.

22 Claims, 8 Drawing Sheets

METHOD FOR IMPLANTING A LAMINOPLASTY

CROSS-REFERENCE TO RELATED APPLICATIONS

This application is a continuation of application Ser. No. 10/260,329, filed Sep. 30, 2002, now U.S. Pat. No. 6,712,852 entitled "Laminoplasty Cage," which is hereby incorporated by reference in its entirety.

FIELD OF THE INVENTION

The present invention relates to spinal implant device, and more particularly to spinal cages useful in laminoplasty surgery.

BACKGROUND OF THE INVENTION

Spinal stenosis is the narrowing of the spinal cord canal, and can result in pain, weakness in arms and/or legs, and unsteadiness in the gait. For mild conditions, conservative treatment may be sufficient. When symptoms are severe or progressive, however, cervical laminoplasty surgery may be required to enlarge the spinal canal to relieve compression of the spinal cord. Common indications which give rise to a need for laminoplasty surgery include stenosis of the spinal canal, ossification of the posterior longitudinal ligament (OPLL), and spondylotic myelopathy.

Surgical techniques used to perform laminoplasty surgery can vary and will depend on many factors, including the source of the spinal cord compression, the number of vertebral segments involved in the disease process, and the cervical alignment. Two common surgical laminoplasty techniques include open door laminoplasty and midline splitting laminoplasty. In open door laminoplasty, the lamina is cut on one side and hinged on the other side. The lamina is then rotated to open the canal, and sutures are placed on the hinged side to maintain the opening. Eventually, bone growth will fill in the gap created on the cut side. In midline splitting laminoplasty, both sides of the lamina are hinged, and the spinous process is bisected into two halves. Both halves are then rotated outwards, and a strut graft is placed between the halves to secure the opening.

Several devices exists for maintaining or stabilizing the lamina in the open or split position. U.S. Pat. No. 6,080,157 of Cathro et al., for example, discloses a device for stabilizing the lamina after open door laminoplasty surgery. The device includes a spacer which is shaped to engage between severed edges of a lamina, and a retainer attached to the spacer which is adapted to maintain the spacer in an operative position. U.S. Pat. No. 6,358,254 of Anderson also discloses a device for expanding the spinal canal. The device includes two stents, two washers, two screws, and a cable. In use, pedicle cuts are made in the vertebra, and a screw is then inserted into each cut, through a washer and a stent, to expand the cut bone. The cable is then attached to each washer and strapped around the posterior portion of the vertebrae to stabilize the expanded canal and allow the vertebrae to heal with the spinal canal expanded.

While these devices have proven effective, they can be difficult to implant, resulting in increased medical costs. Moreover, the devices do not have a substantially low-profile, and thus can potentially cause damage to surrounding tissue and/or to the spinal cord. The devices are also not designed to restore the natural dynamics of the cervical spine, and thus can cause discomfort to the patient.

Accordingly, there exists a need for an improved laminoplasty implant that is effective to maintain and stabilize the position of the lamina after laminoplasty surgery. Moreover, there is a need for a device that can be easily and safely implanted, that will allow for permanent bony incorporation when used with bone growth promoting materials, that will allow for muscle re-attachment, and that will restore the natural dynamics of the cervical spine.

SUMMARY OF THE INVENTION

The present invention provides a medical implant device having a hollow elongate body including a longitudinal axis, opposed cephalad and caudal sides, and opposed posterior and anterior sides adjacent to the cephalad and caudal sides. The cephalad, caudal, posterior, and anterior sides define an inner lumen having opposed first and second open ends. The implant can be used for a variety of applications, but is preferably used to stabilize and maintain the position of a bisected spinous process after laminoplasty surgery.

In one embodiment, at least one of the cephalad side, the caudal side, and the posterior side includes at least one perforation formed therein, and the anterior side of the body is perforation-free. Preferably, the cephalad side, the caudal side, and the posterior side each include a several perforations formed therein. The perforations can have a variety of shapes and size, but are preferably elongated slots extending in a direction transverse to the longitudinal axis of the of the elongate body. The slots can optionally include a suture-receiving recess formed therein for retaining suture.

In another embodiment, the anterior side of the implant includes a first edge mated to the cephalad side and a second edge mated to the caudal side. Preferably, the first and second edges of the anterior side are substantially rounded. The anterior side of the elongate body can also be curved along the longitudinal axis such that an outer surface of the anterior side is concave. The rounded edges and the curved anterior side prevent potential abrasion or damage to tissue surrounding the implant, and provide additional space for the spinal cord in the spinal canal. The entire elongate body can also be curved along the longitudinal axis such that an outer surface of the anterior side is concave, and an outer surface of the posterior side is convex. That is, the planes defined by the first and second open ends are converging. This can be effected by designing the elongate body with the posterior side being longer than the anterior side.

In another embodiment, the elongate body preferably has an anatomical cross-section extending in a direction transverse to the longitudinal axis, such that the cross-section of the elongate body conforms to the shape of a patient's bisected spinous process. By way of non-limiting example, the cross-section can be in the shape of a parallelogram, a square, a rectangle, a diamond, an oval, and a circle. The first and second open ends of the elongate body can also have an anatomical shape such that they are adapted to be positioned between a split spinous process of a patient's spinal system. Preferably, the first and second open ends are angled with respect to the longitudinal axis.

In another embodiment, the elongate body includes first and second halves positioned on opposed sides of a midpoint of the body. The first and second halves are preferably angled with respect to one another, such that the implant is bent at the midpoint. The bend is effective to provide additional space for the spinal cord within the spinal canal.

In other aspects of the invention, the implant can include a spinous process replacement member extending outward from the body in a direction transverse to the longitudinal axis. In another embodiment, the implant can include at least one radiopaque member disposed therein and configured to provide an x-ray visible reference to indicate the position of the implant with respect to an anatomical structure when the implant is positioned within an interstitial space.

In yet another embodiment of the present invention, a medical implant device is provided having a hollow elongate body including a longitudinal axis, opposed cephalad and caudal sides, and opposed posterior and anterior sides adjacent to the cephalad and caudal sides. The cephalad side, caudal side, posterior side, and anterior side define an inner lumen having opposed first and second open ends. The implant further includes a fixation element receiving member mated to the posterior side of the implant, adjacent the first open end. The fixation element receiving member extends at an angle with respect to the longitudinal axis and is effective to receive a fixation element for attaching the implant to a bone structure.

In other aspects, the posterior and anterior sides of the implant have a length extending along the longitudinal axis greater than a length of the cephalad and caudal sides, and the cephalad and caudal sides each include a concave recess formed adjacent each of the first and second ends, such that the first and second ends are adapted to seat a bone structure. The anterior side of the implant, adjacent the first open end, can also include an extension member opposed to the fixation element receiving member.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention provides a medical implant device for use in spinal surgery, and more preferably for use in laminoplasty surgery. The implant is a cage-like member having a generally hollow, elongate body with open ends. The implant can be adapted for use in a variety of applications, but is preferably used to maintain the position of vertebra after midline or open door laminoplasty surgery. The implant is particularly advantageous in that it is easy to implant, it will allow for permanent bony incorporation when used with bone growth promoting materials, it will allow for muscle re-attachment, it will restore the natural dynamics of the cervical spine, and it has a substantially low-profile to avoid or prevent damage to surrounding tissue.

Figure 1:
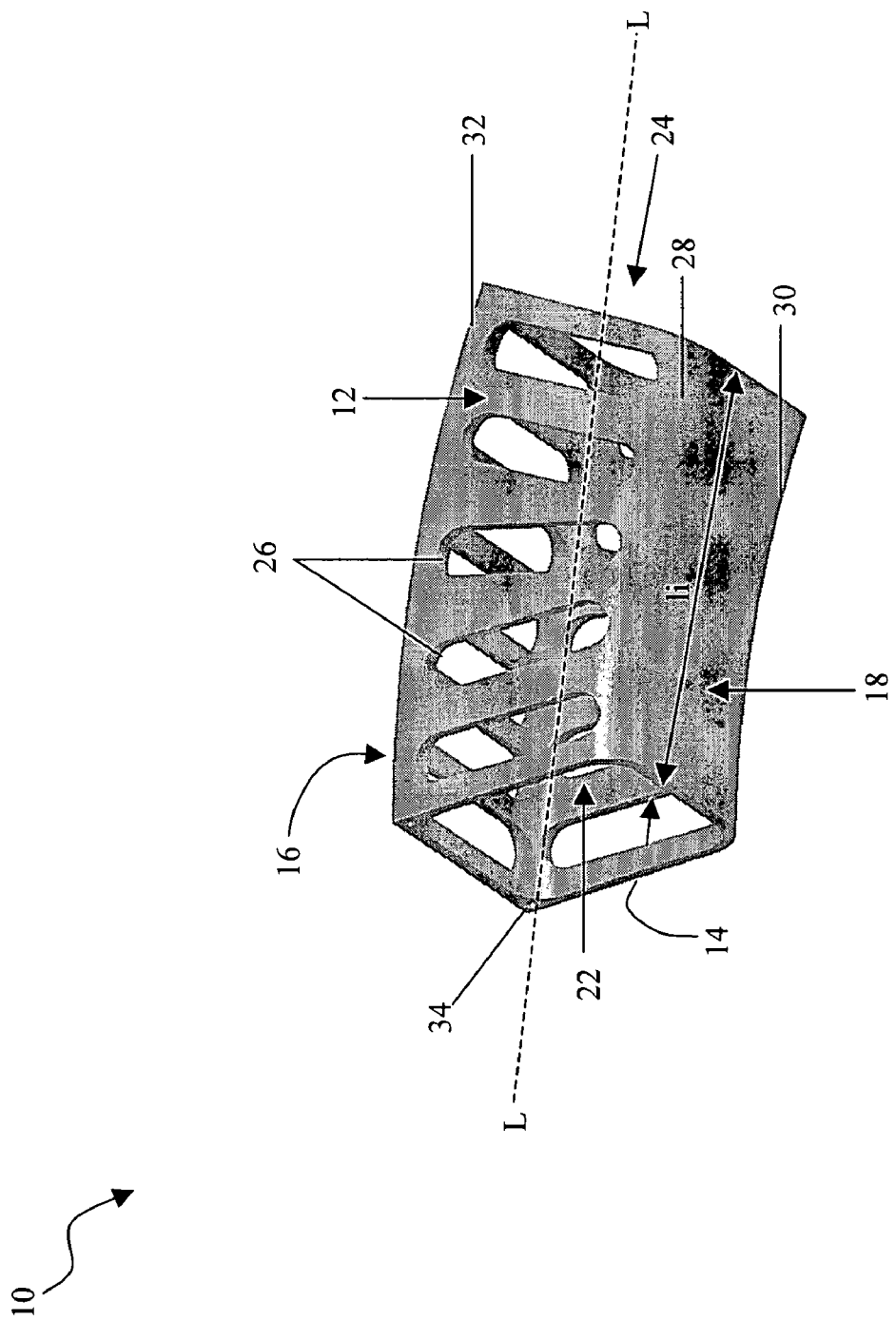
FIG. 1 is an anterior-cephalad perspective view of an implant according to one embodiment of the present invention.
Figure 2:
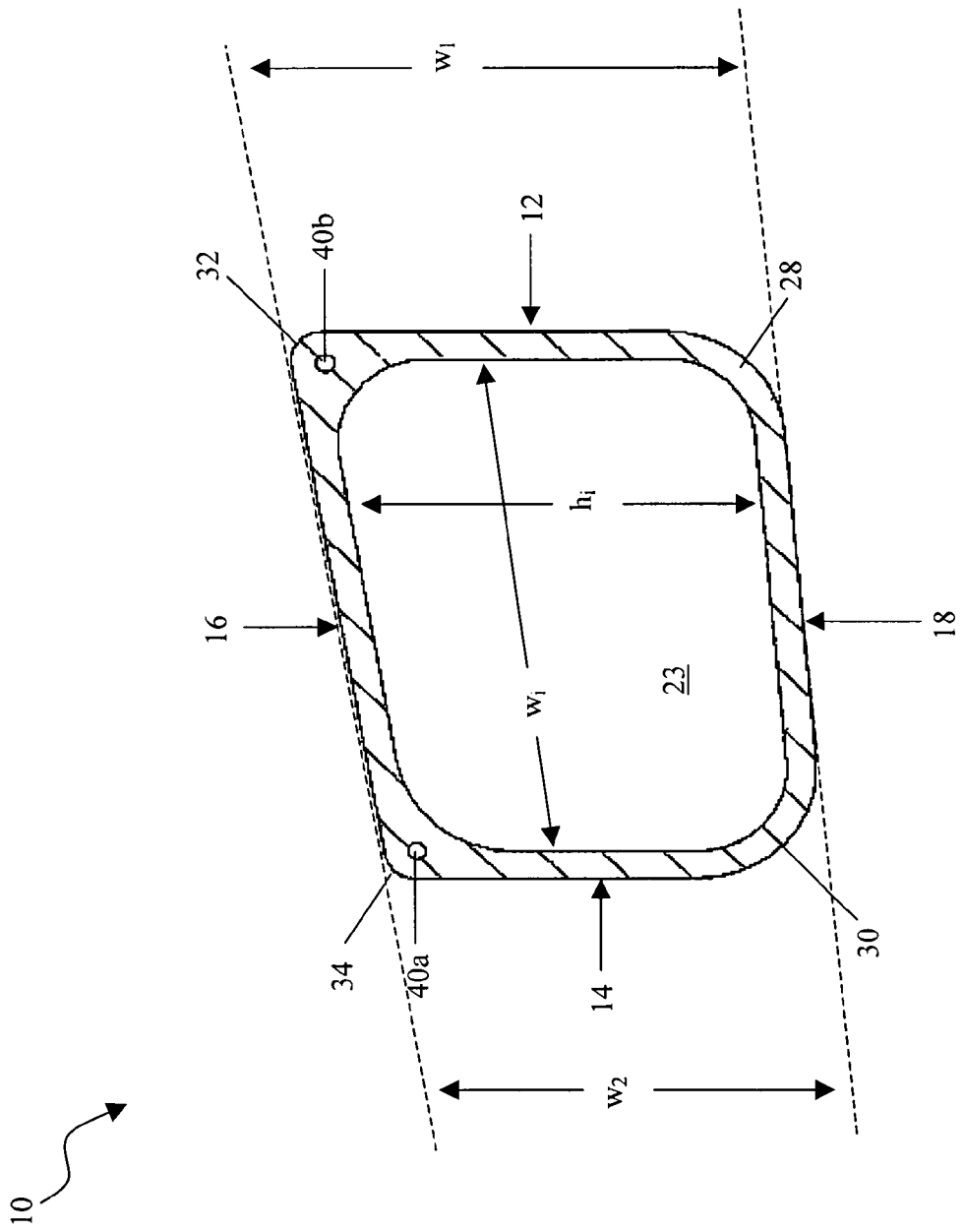
FIG. 2 is an end view of the implant shown in FIG. 1.

FIGS. 1 and 2 illustrate one embodiment of an implant 10 according to the present invention. The implant 10 can have a variety of shapes and sizes, but preferably has a size and a geometry that enables it to be positioned in a bisected spinous process, and to remain securely positioned until healing and fusion take place. Moreover, the implant 10 preferably has a substantially low profile to prevent potential abrasion or damage to surrounding tissue. As shown in FIG. 1, the implant 10 is formed from a generally hollow, elongate body having four sides: opposed cephalad and caudal sides 12, 14, and opposed posterior and anterior sides 16, 18 adjacent to the cephalad and caudal sides 12, 14. The implant 10 has a longitudinal axis L and the four sides 12, 14, 16, 18 define an inner lumen 23 (FIG. 2) extending between opposed first and second open ends 22, 24. The sides 12, 14, 16, 18 of the implant 10 can be substantially planar, or can be curved along the longitudinal axis L depending on the intended use. As shown in FIG. 1, the implant 10 is curved along the longitudinal axis L toward the anterior side 18, such that the outer surface of the anterior side 18 has a concave shape. Since the anterior side 18 is adapted to face a patient's spinal cord when implanted, the curved shape of the implant 10 will provide additional clearance for the spinal cord. A person having ordinary skill in the art will appreciate that the shape of each side 12, 14, 16, 18 can vary, and that all four sides 12, 14, 16, 18 can have different configurations.

The implant 10 can also have a variety of cross-sectional shapes extending in a direction transverse to the longitudinal axis. By way of non-limiting example, the cross-section can be in the shape of a square, a rectangular, a circle, an oval, a diamond, and a triangle. Preferably, the implant has a cross-section that is adapted to contour the shape of a bisected spinous process. FIG. 2 illustrates an end view of implant 10 have a cross-section in the shape of a parallelogram. As shown, the caudal side 12 has a width $w_1$ greater than a width $w_2$ of the cephalad side 14, such that the height $h_i$ of the implant 10 between the posterior and anterior sides 16, 18 increases from the cephalad side 14 to the caudal side 12. The anatomical shape of the implant reduces impingement with adjacent bone structures and grafts, facilitates the secure positioning of the implant, and increases the patient's range of motion. The open ends 22, 24 of the implant 10 are also preferably adapted to contour the shape of a bisected spinous process. Preferably, each end 22, 24 is angled to match the angle of the cut ends of the bisected spinous process. That is, the planes defined by the first and second open ends 22, 24 are converging. This can be effected by designing the elongate body with the posterior side 16 being longer than the anterior side 18.

The implant 10 can also be adapted to prevent potential abrasion or damage to surrounding tissue. Still referring to FIGS. 1 and 2, the implant 10 includes four edges 28, 30, 32, 34 extending between each side 12, 14, 16, 18. The first edge is positioned between the anterior side 18 and the caudal side 12, and the second edge is positioned between the anterior side 18 and the cephalad side 14. The first and second edges 28, 30 are preferably substantially rounded to prevent potential abrasion or damage to the spinal cord and tissue surrounding the implant 10. The third and fourth edges 32, 34, which are positioned between the posterior side 16 and the caudal side 12, and the posterior side 16 and the cephalad side 14, respectively, can have any shape, as they are not positioned adjacent the spinal cord when implanted. Preferably, the third and fourth edges 32, 34 have a slightly rounded profile.

The dimensions of the implant 10 can also vary depending on the intended use. Preferably, the implant 10 has a length $l_i$ (FIG. 1), width $w_i$ (FIG. 2), and height $h_i$ (FIG. 2) that is sufficient to fit within a bisected spinous process and to provide the necessary expansion of the spinal canal. More preferably, the implant 10 has a length $l_i$ extending between the first and second open ends 22, 24 that is in the range of about 8 mm to 25 mm, a height $h_i$ extending between the posterior and anterior sides 16, 18 that is in the range of about 4 mm to 10 mm, and a width $w_i$ extending between the caudal and cephalad sides 12, 14 that is in the range of about 5 mm to 15 mm. A person having ordinary skill in the art will appreciate that the dimensions of the implant can vary depending on the intended use.

Referring back to FIG. 1, the implant 10 can also include one or more perforations 26 formed therein for facilitating secure placement and fusion of the implant 10 within the split spinous process. The perforations 26 can have any shape and size, and can be formed in one or more of the sides 12, 14, 16, 18, of the implant 10. Preferably, the anterior side of the implant 18 is perforation-free to prevent potential abrasion or other damage to the dura mater, and the remaining three sides 12, 14, 16 each preferably include one or more perforations 26 formed therein. While the size, shape, and placement of each perforation 26 can vary, the perforations 26 are preferably in the form of elongated slots extending in a direction transverse to the longitudinal axis L of the implant 10. Each slot 26 should have a size and shape sufficient to allow for vascularization of the implant, the placement of bone growth promoting materials inside the implant, as well as muscle re-attachment to the bone growth promoting materials. In an exemplary embodiment, shown in FIG. 4, at least one of the slots 126 formed in the implant 100 can include a suture-receiving recess 127. The recess 127 is effective to receive sutures used to secure the implant 100 to surrounding bone, and to prevent the sutures from sliding within the slot 126. A person having ordinary skill in the art will appreciate that a variety of techniques can be used to secure suture to the implant, and to secure the implant to the adjacent bone structure.

Figure 3:
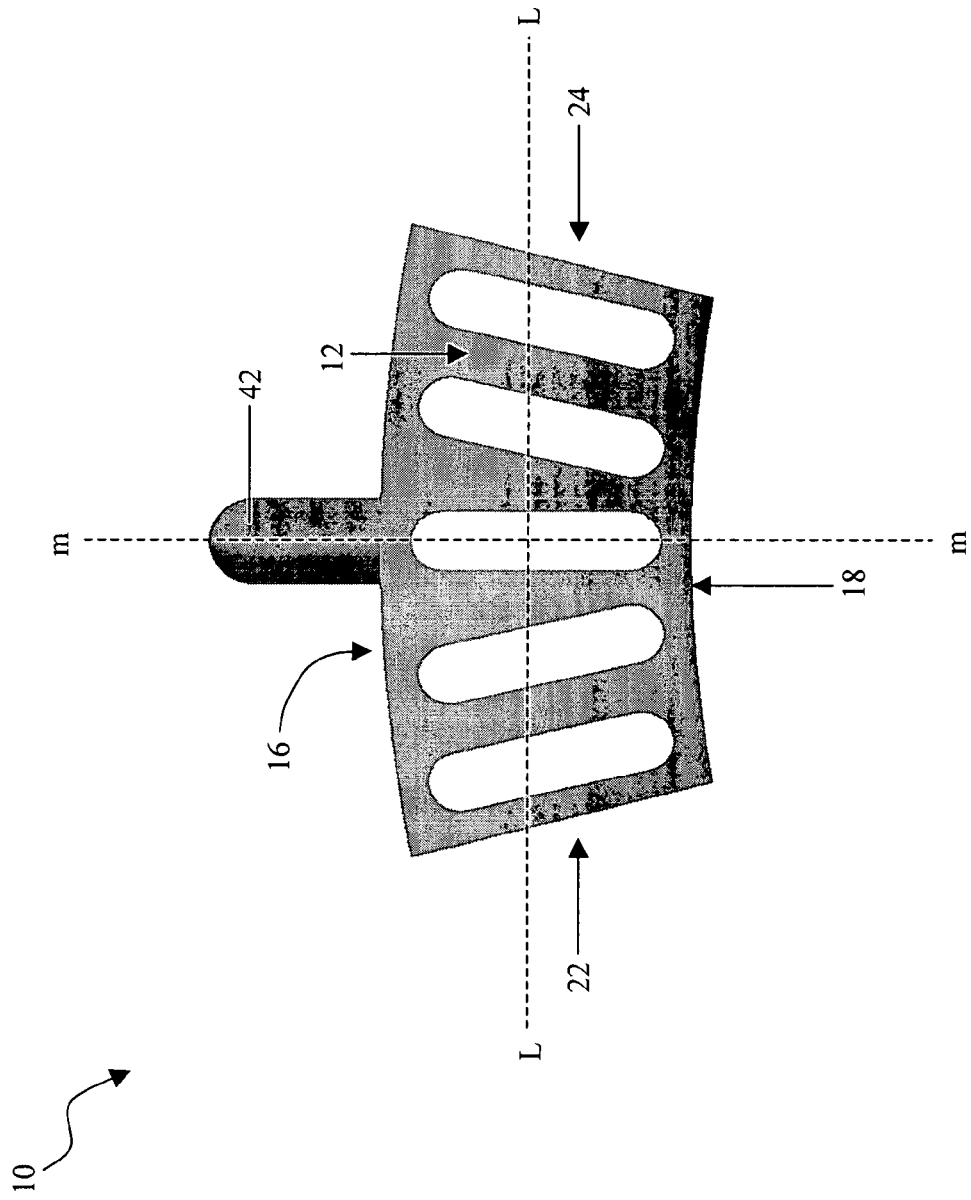
FIG. 3 is a cephalad side view of the implant shown in FIG. I having a spinous process replacement member.

FIG. 3 illustrates another embodiment of the implant 10 shown in FIG. 1 having a spinous process replacement member 42. The replacement member 42 is effective to allow for muscle re-attachment and will restore the natural dynamics of the cervical spine. The replacement member 42 can have a variety of configurations, but should conform to the natural shape of the spinous process. Preferably, the replacement member 42 is preferably a rigid elongate member that extends outward from the implant in a direction transverse to the longitudinal axis L. The replacement member 42 should be mated to or disposed on the posterior side 16 of the implant 10, and should be positioned at a midpoint m, shown along line m-m. The replacement member 42 can be solid or hollow, and can optionally include one or more perforations (not shown) formed therein.

The replacement member 42 can be permanently or removably attached to the implant 10. Where the implant 10 is removably attached, the replacement member 42 can be mated to the posterior side 16 of the implant 10 using any type of fastening element, such as, for example, threads which engage similar threads formed on a bore extending into the posterior side 16 of the implant 10, or a taper post matable with a taper bore disposed in the posterior side 16. A person having ordinary skill in the art will readily appreciate that the replacement member 42 can be disposed on or attached to the implant 10 using a variety of different techniques.

Figure 4:
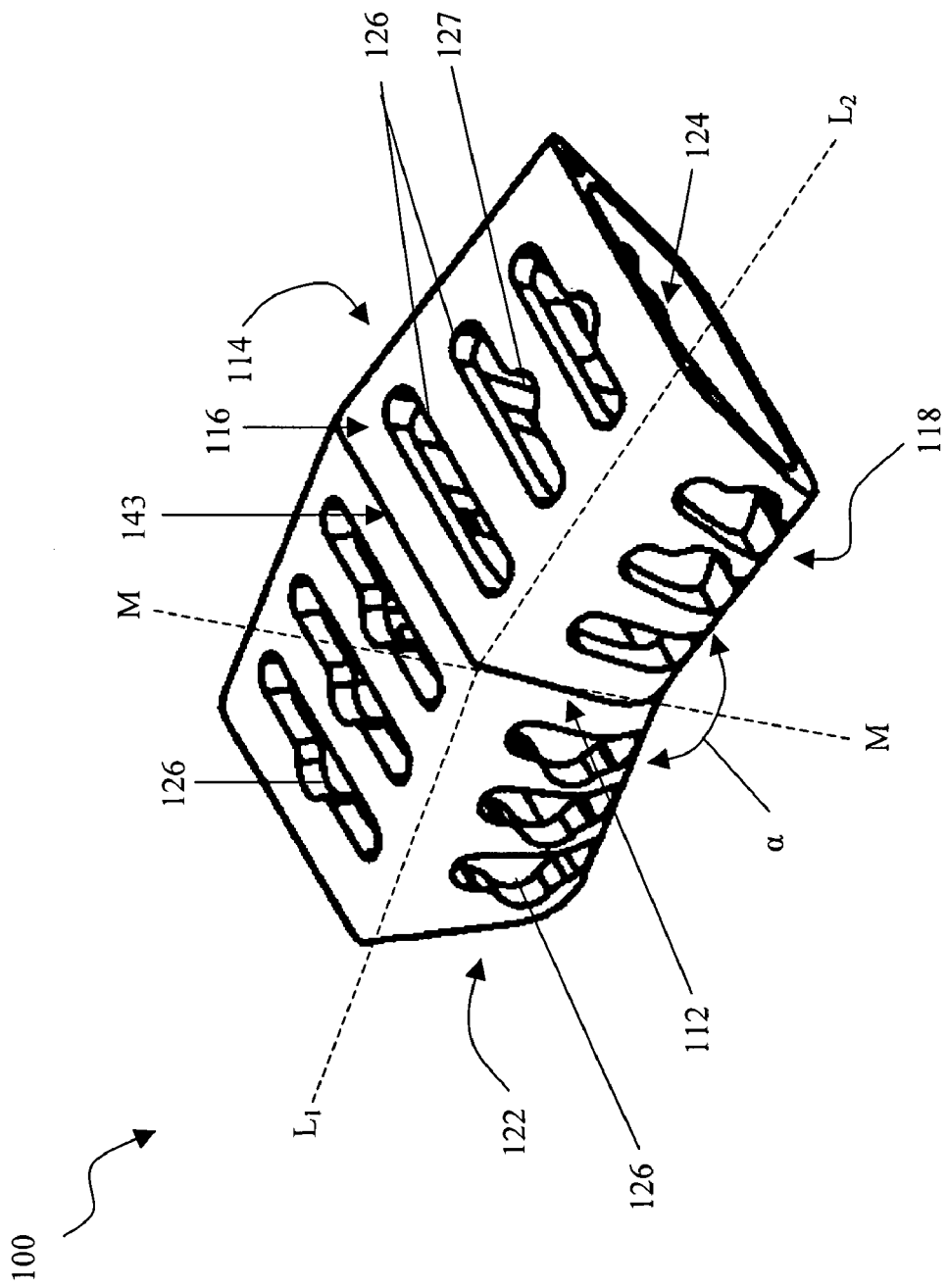
FIG. 4 is posterior-cephalad perspective view of another embodiment of an implant according to the present invention.

FIG. 4 illustrates another embodiment of an implant 100 having opposed caudal and cephalad sides 112, 114, and opposed posterior and anterior sides 116, 118 adjacent the caudal and cephalad sides 112, 114. The implant 100 is similar to implant 10, but includes a bend 143 formed at a midpoint M, shown as line M-M. The bend 143 is directed toward the anterior side 118 of the implant, such that the two halves of the anterior side 118, extending from the midpoint M, are bent toward one another. As a result, the implant includes two longitudinal axis $L_1$, $L_2$ extending from the midpoint M. The angle α of the bend 143, measured at the anterior side 143, can vary depending on the intended use, but preferably the bend 143 has an angle a in the range of about 150° to 170°. In use, the bend 143 is effective to provide additional space for the spinal cord. More preferably, the bend 143 provides about 0.5 mm to 2.5 mm more space for the spinal cord.

Figure 5:
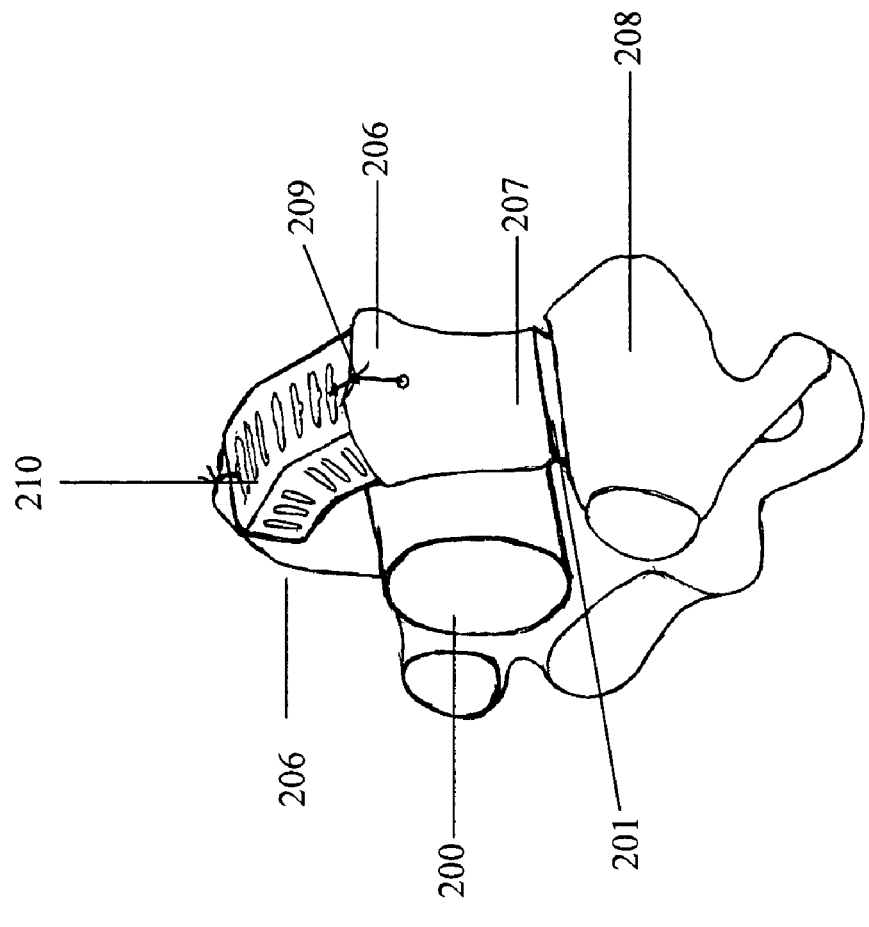
FIG. 5 is perspective view of an implant according to the present invention positioned in a patient's spinal column after laminoplasty surgery.

FIG. 5 illustrates an implant 200, representative of an implant according to the present invention, disposed within a bisected spinous process 206 of a vertebra 204 in a patient's spinal column. The spinous process 206 is prepared by forming a cut through the bone to separate the spinous process 206 into two halves. A small incision 201 is then formed on each side of the spinous process 206 between spinous articular process 207 and the transverse process 208. The incision 201 is effective to form a hinge to allow the bisected spinous process 206 to be opened. The implant 200 is then positioned between the bisected spinous process 206, thereby enlargening the spinal canal to relieve compression on the spinal cord 210. A person having ordinary skill in the art will appreciate that a variety of techniques can be used for securing the implant 200 to the adjacent bone.

By way of non-limiting example, the implant 200 can be secured in place using sutures or other securing techniques known in the art. Preferably, as shown in FIG. 5, a suture 209 is inserted through one side of the bisected spinous process 206, through the inner lumen of the implant 200, and then through the other side of the bisected spinous process 206. The suture 209 is then tied to prevent movement of the implant 200 with respect to the vertebra 204. The implant can also optionally include bone growth promoting materials disposed therein for promoting fusion of the implant to the spinous process. Preferably, the inner lumen of the implant is packed with morsellized bone graft.

In order to facilitate placement of an implant in a split spinous process, the implant can optionally include one or more radiopaque markers disposed therein. The radiopaque markers are configured to provide an x-ray visible reference to indicate the position of the implant with respect to an anatomical structure when the implant is positioned within an interstitial space. The markers can have virtually any configuration, and can be positioned around and/or within the implant. The position of the markers should be adapted to facilitate accurate placement of the implant in the split spinous process. Referring back to FIG. 2, the implant 10 is shown having markers 40a and 40b extending along edges 32 and 34. The markers 40a, 40b are each in the form of an elongate wire, and are disposed within the body of the implant 10. Preferably, the body of the implant 10 is formed from a radiolucent material to allow the radiopaque markers to be distinguished from the implant 10 in an x-ray image.

Figure 6:
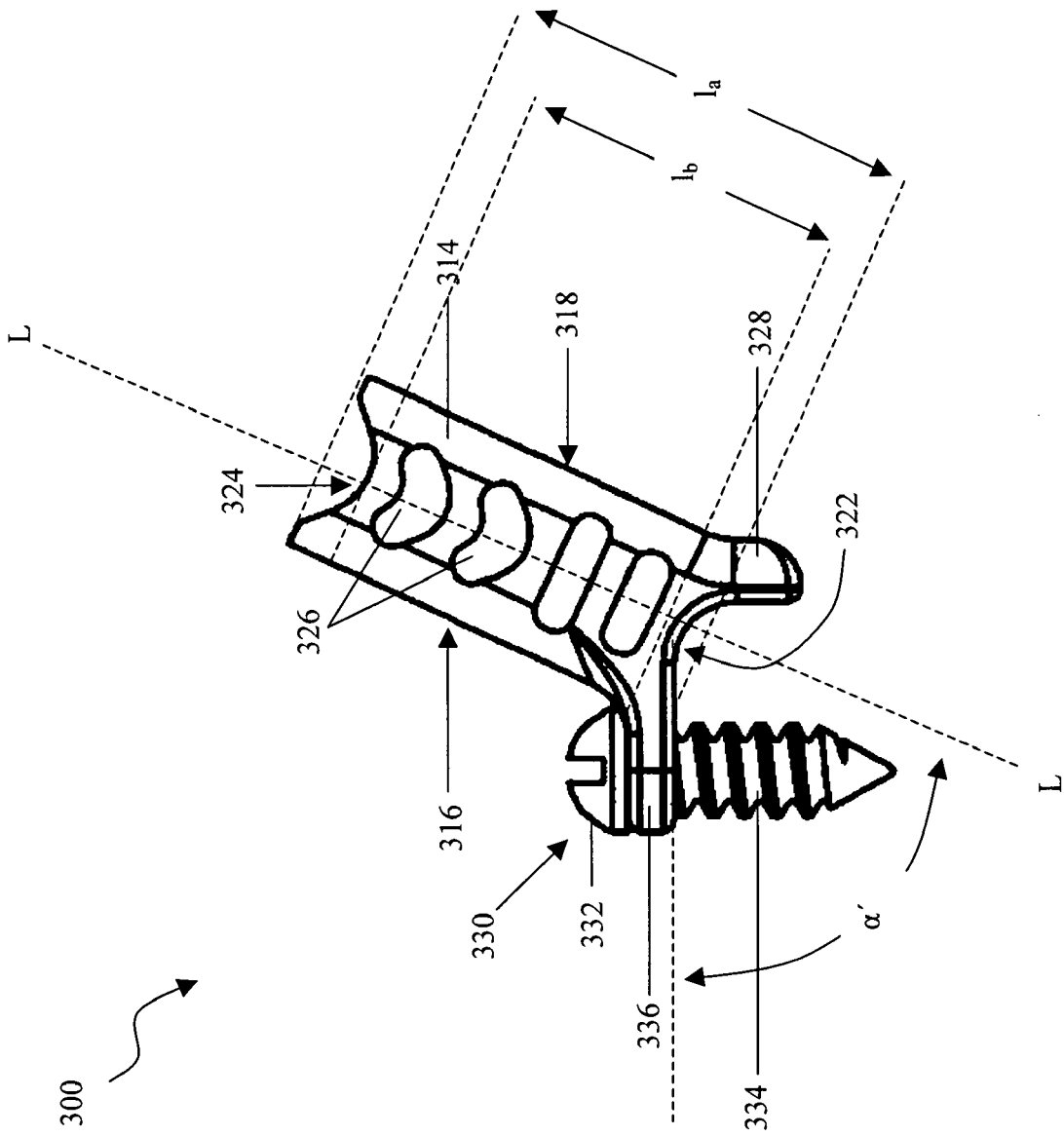
FIG. 6 is a cephalad side view of another embodiment of an implant having a fixation element receiving member.
Figure 7:
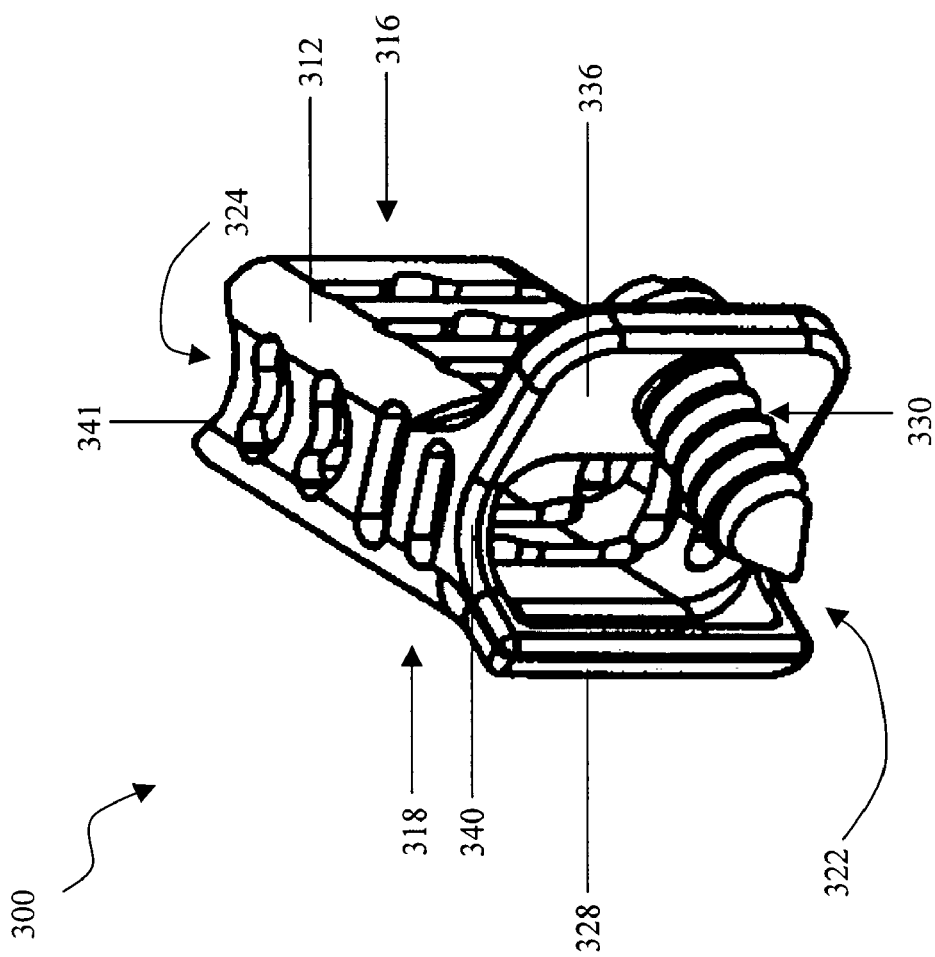
FIG. 7 is an end view of the implant of FIG. 6.

FIGS. 6 and 7 illustrate another embodiment of an implant 300 preferably for use in open-door laminoplasty surgery. The implant 300 is similar to implant 10 shown in FIG. 1 and includes opposed cephalad and caudal sides 312, 314, and opposed posterior and anterior sides 316, 318 adjacent to the cephalad and caudal sides 312, 314. The four sides 312, 314, 316, 318 extend along a longitudinal axis L, and define an inner lumen 323 (FIG. 7) extending between opposed first and second open ends 322, 324. While the implant 300 is shown having an inner lumen 323 formed therein, the implant 300 can alternatively be a solid, elongate member.

The implant 300 can have a variety of shapes and sizes, and can be substantially planar, curved, or bent. Preferably, the caudal, cephalad, posterior, and anterior sides 314, 314, 316, 318 are substantially planar and form a rectangular or substantially square elongate member. The posterior and anterior sides 316, 318 can have a length $l_a$ greater than a length $l_b$ of the caudal and cephalad sides 312, 314. The difference in length is effective to form a concave recess 340 in each open end 322, 324 of the implant 300. In use, the concave recess 340 is adapted to seat, and optionally engage and/or conform to, a portion of a bone structure to facilitate the secure placement of the implant 300 between the bisected bone structure. The implant 300 can also optionally include one or more perforations 326, similar to perforations 26 disclosed above with reference to FIG. 1, formed in one or more sides 312, 314, 316, 318 of the implant 300. Preferably, the perforations 326 are formed in the caudal, cephalad, and posterior sides 312, 314, 316, and the anterior side 318 is perforation-free to protect the spinal cord.

The implant 300 can also include a fixation element receiving member 336 mated to the posterior side 316 of the implant 300 that is effective to receive a fixation element, such as a bone screw 330 or a suture material, for attaching the implant 300 to a bone structure. The receiving member 336 can have a variety of configurations, but is preferably an extension of the posterior side 316. The receiving member 336 can have a substantially planar shape, can be angled, or can have some other shape. While FIGS. 6 and 7 illustrate the receiving member 336 formed adjacent the first open end 322, the receiving member 336 can be formed on either one or both of the first and second ends 322, 324. Preferably, the receiving member 336 is disposed at an angle α' with respect to the longitudinal axis. The angle α' can vary depending on the intended use, but preferably the receiving member 336 extends from the posterior side 316 in the posterior direction at an angle α', relative to the longitudinal axis, in the range of about 35° to 75°, as measured in a direction toward the first open end 322.

The receiving member 336 can include a bore 337 formed therein for receiving a fixation element. By way of non-limiting example, FIGS. 6 and 7 illustrate bone screw 330 disposed within the bore 337 in the receiving member 336. The bone screw 330 includes a head 332 positioned on one side of the bore 337, and a shank 334 disposed through the bore 337. The shank 334 includes threads formed thereon for threading the bone screw 330 into a bone structure. A person having ordinary skill in the art will appreciate that a variety of fixation elements can be used with the implant 300.

The implant 300 can also include an extension member 328 formed on the anterior side 318 adjacent the first open end 322, and opposed to the receiving member 336. The extension member 328 can also be substantially planar, or can be positioned at an angle with respect to the longitudinal axis L in a direction opposed to the receiving member 336. The extension member 338 is effective to facilitate the secure placement of the implant 300 between a bisected bone structure. More particularly, the extension member 338 should be sufficient to prevent the implant 300 from becoming dislodged during insertion of the fixation element 330 into the bone structure.

Figure 8:
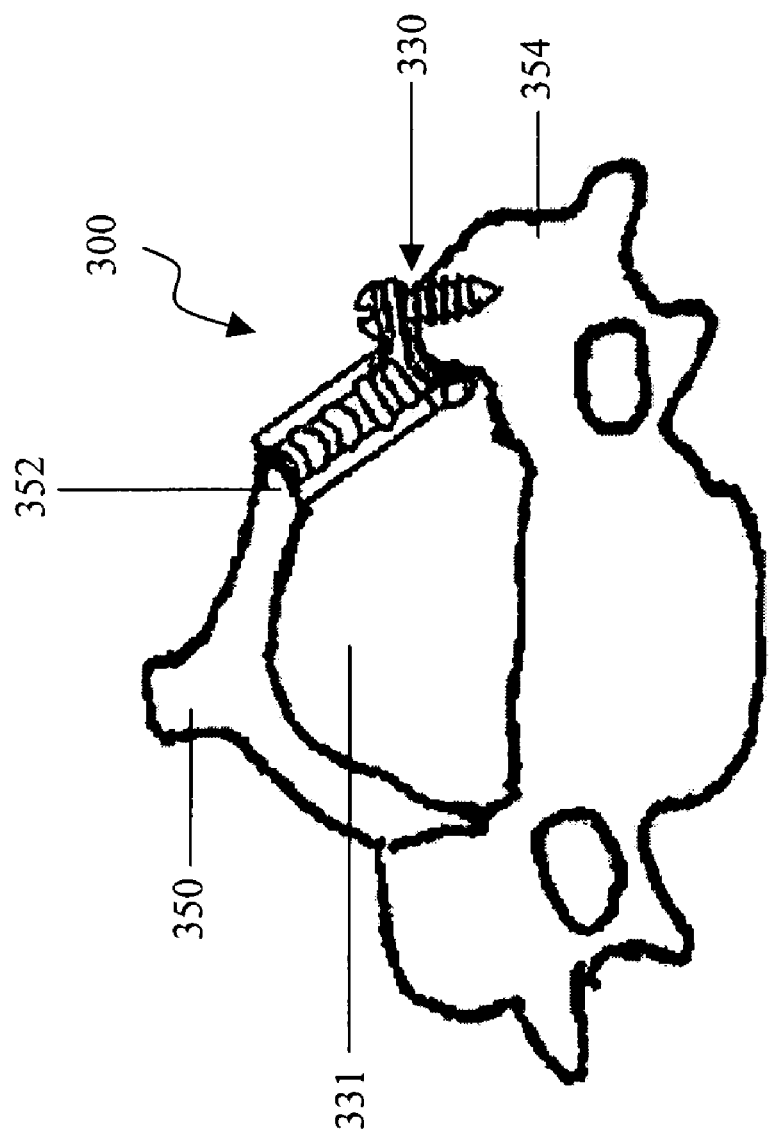
FIG. 8 is an illustration showing the implant of FIG. 6 positioned within a bisected vertebra.

FIG. 8 illustrates the implant 300 in use disposed within a vertebra 360 of a patient's spinal column. The implant 300 is positioned between a bisected lamina 354 of the vertebra 360, thereby enlarging the spinal canal 331. The fixation device, e.g., the bone screw 330, is disposed through the bore formed in the receiving member 336 and threaded into the lamina 354 to secure the position of the implant 300 with respect to the vertebra 360.

While not illustrated, an implant according to the present invention can include a variety of other features to facilitate placement of the implant in the split spinous process or lamina. By way of non-limiting example, the implant can include a number of bone engaging surface features formed on the end surfaces. The bone engaging surface features are preferably adapted to engage the cut portion of the split spinous process or lamina to facilitate the secure placement of the implant. In another embodiment, the implant can be adapted to mate to an insertion tool for inserting the implant into the split spinous process. For example, the implant can be used in conjunction with a distractor or spreader device. A person having ordinary skill in the art will appreciate that a variety of insertion tools can be used with the implant of the present invention, and that the implant can be modified to work with such a tool.

The materials used for form a laminoplasty cage according to the present invention can vary. Preferably, the body is formed from a rigid, semi-rigid, or flexible radio-lucent material. More preferably, the body is formed from materials such as polymers, ceramics, composite materials, and combinations thereof. Examples of suitable polymers include polyether sulfone, polycarbonate, bioabsorbable polymers, polyaryletherketones, and carbon fiber reinforced polymers. The implant can alternatively, or in addition, be formed from a variety of metals, including titanium, titanium alloys, chrome alloys, and stainless steel.

The marker strip can also be formed from a variety of radiopaque materials including, for example, metals, polymers, filling salts, ceramics, and combinations thereof. Examples of suitable metals include titanium, stainless steel, tantalum, cobalt chromium, aluminum, and combinations thereof. A person having ordinary skill in the art will appreciate that the body can be formed from a radiopaque material, and the marker strip can be formed from a radio-lucent material.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for implanting a medical device, comprising:
   forming at least one cut in a portion of a vertebra of a patient's spine to separate the vertebra into at least two halves; and
   positioning opposed ends of an elongate body between two halves of the vertebra to enlarge a spinal canal formed within the vertebra such that a slot-free anterior side is positioned adjacent to the spinal canal and a plurality of elongate slots formed in cephalad, caudal, and posterior sides of the elongate body are positioned away from the spinal canal.

2. The method of claim 1, wherein a first cut is formed in a spinous process of a vertebra of a patient's spine to separate the spinous process into two halves that seat the elongate body therebetween, and wherein at least one of a second and third cut is formed on a side of the spinous process between the spinous articular process and the transverse process to form a hinge that is effective to allow the two halves of the spinous process to be separated.

3. The method of claim 2, wherein the elongate body is hollow, and the opposed open ends of the hollow elongate body are positioned adjacent to the two halves of the spinous process.

4. The method of claim 3, wherein the open ends are angled such that planes defined by the first and second ends converge.

5. The method of claim 3, wherein the hollow elongate body has an anatomical cross-section extending in a direction transverse to a longitudinal axis extending between the opposed open ends, such that the cross-section of the hollow elongate body conforms to the shape of the two halves of the spinous process.

6. The method of claim 5, wherein the cross-section of the hollow elongate body has a shape selected from the group consisting of a parallelogram, a square, a rectangle, a diamond, an oval, and a circle.

7. The method of claim 1, wherein the posterior and anterior sides have a length extending along the longitudinal axis that is greater than a length of the cephalad and caudal sides.

8. The method of claim 1, wherein each slot extends in a direction transverse to the longitudinal axis of the elongate body.

9. The method of claim 8, wherein at least one of the slots includes a suture-receiving recess formed therein that is effective to receive and prevent movement of a suture disposed within the slot, and wherein the method further comprises the step of passing at least one suture through at least one of the slots such that the at least one suture is positioned within at least one suture-receiving recess, and attached the suture to bone adjacent to the hollow elongate member to anchor the hollow elongate member to the patient's vertebra.

10. The method of claim 1, wherein the anterior side of the elongate body is curved such that an outer surface of the anterior side is concave.

11. The method of claim 1, wherein the elongate body is curved such that an outer surface of the anterior side is concave, and an outer surface of an opposed posterior side is convex.

12. The method of claim 1, wherein the elongate body includes first and second halves positioned on opposed sides of a midpoint of the hollow elongate body, the first and second halves being angled with respect to one another.

13. A method for implanting a medical device, comprising:
cutting a spinous process in a patient's vertebra to form a bisected spinous process having two halves;
separating the two halves of the bisected spinous process; and
positioning an elongate body between the two halves of the bisected spinous process to enlarge a spinal canal formed within the vertebra and to position a spinous process replacement member extending outward from the elongate body at a location in which the spinous process replacement member mimics the spinous process before it is bisected.

14. The method of claim 13, wherein the spinous process replacement member has a shape that conforms to a natural shape of the spinous process.

15. The method of claim 13, further comprising the step of attaching muscle separated from the spinous process to the spinous process replacement member.

16. A method for implanting a medical device, comprising:
cutting a lamina in a patient's vertebra such that a spinous process and a spinous articular process of the vertebra are separated from one another; and
positioning an elongate body between the separated spinous process and spinous articular process such that a fixation element receiving member extending outward from a first end of the elongate body is positioned adjacent to the a posterior side of the spinous articular process, and an extension member formed on the elongate body and opposed to the fixation element receiving member is positioned adjacent to an anterior side of the spinous articular process;
passing at least one suture through at least one slot formed in the elongate body such that the at least one suture is positioned within at least one suture-receiving recess formed in the at least one slot; and
attaching the at least one suture to bone adjacent to the elongate body to anchor the elongate body to the vertebra.

17. The method of claim 16, further comprising the step of attaching the fixation element receiving member to the spinous articular process using a fixation element.

18. The method of claim 17, wherein the fixation element receiving member includes a bore formed therein, and wherein the fixation element comprises a bone screw, and wherein the step of attaching the fixation element receiving member to the spinous articular process comprises threading the bone screw through the bore and into the spinous articular process.

19. The method of claim 16, wherein the fixation element receiving member and the extension member each extend at an angle away from one another with respect to a longitudinal axis of the elongate body that extends between opposed first and second ends of the elongate body.

20. The method of claim 19, wherein the fixation element receiving member extends in a posterior direction at an angle, relative to the longitudinal axis, in the range of about 35° to 75°.

21. The method of claim 16, wherein a first concave recess is formed in the first end of the elongate body between the fixation element receiving member and the extension member, and the first recess seats a portion of the spinous articular process.

22. The method of claim 21, further comprising a second concave recess formed in a second, opposed end of the elongate body, the second concave recess seating a portion of the cut lamina adjacent to the spinous process.

* * * * *